United States Patent [19]
Daniels

[11] Patent Number: 4,643,932
[45] Date of Patent: Feb. 17, 1987

[54] LAMINATED FASTENING STRAP

[76] Inventor: Jerry Daniels, 4308 Ooltewah-Ringgold Rd., Ooltewah, Tenn. 37363

[21] Appl. No.: 803,650

[22] Filed: Dec. 2, 1985

[51] Int. Cl.⁴ .............................................. A41F 9/00
[52] U.S. Cl. ..................................... 428/100; 2/338; 2/DIG. 6; 128/68; 128/DIG. 15
[58] Field of Search ............................. 2/DIG. 6, 338; 128/DIG. 15, 68, 169; 428/100

[56] References Cited

U.S. PATENT DOCUMENTS 3,013,919 12/1961 Bialy ..................................... 2/338 X
3,086,529 4/1963 Munz et al. .......................... 2/338 X
3,112,496 12/1963 Dritz ..................................... 2/338 X
3,574,019 4/1971 Girard .............................. 428/100 X
4,091,808 5/1978 Nelson ........................ 128/DIG. 15
4,127,120 11/1978 Applegate .................. 128/DIG. 15

Primary Examiner—Henry F. Epstein
Attorney, Agent, or Firm—Alan Ruderman

[57] ABSTRACT

A laminated fastening strap has synthetic hook and loop fastening elements formed on one sheet of the laminate and has a vinyl backing formed on the other sheet. The sheets are laminated together by bonding utilizing dielectric bonding apparatus. The bonds between the sheets are along the borders of the strap and along areas extending transverse to the longitudinally extending borders and angularly extending bond areas. The angularly extending bonds permits cutting along a desired diagonal so as to shorten the strap as required thereby permitting the use of straps of a conventional size which may be cut to the required necessary size only when needed.

5 Claims, 4 Drawing Figures

LAMINATED FASTENING STRAP

BACKGROUND OF THE INVENTION

This invention relates to fastening straps and more particularly to straps used in conjunction with orthopedic appliances and athletic equipment, the straps having synthetic material fastening elements which adhere when pushed together and a vinyl backing.

Straps used in conjunction with orthopedic wearing appliances and the like generally have interlockable hook and loop fastening elements. In one type, known as a face strap, one of the elements is attached to a first portion of the appliance and the other elements are adapted to pass through a ring fastened to a second portion of the appliance so that it may be drawn back toward the first portion and connect with the element on the first portion. In another type, known as a back strap, the hook and loop elements face in opposite directions and no ring is required. In either manner the two portions of the appliance may be securely connected together. For example, a brace or orthopedic corset may be so constructed to be adjustably worn by a patient or the like.

It is known in the prior art to use fasteners comprising synthetic materials which adhere when pressed together such as that sold under the trademark VELCRO, i.e., interlocking plastic hooks and tiny pile-like loops which effectively concatenate when pushed together to engage and which may be readily pulled apart to disengage. These fastening elements, hereinafter referred to as synthetic hook and loop fastener elements, in the prior art are bonded by ultrasonic means to backing strips of fabric textile material to form the strap, the ultrasonic process being such that relatively low heat is generated. However, such machines that exist for ultrasonic bonding can only bond one strap at a time and thus the process is very labor intensive. The large size of the machinery and the amount of power necessary to ultrasonically bond a number of such items in gang fashion has made this economically and functionally impractical. Thus, the cost of manufacturing such straps remains relatively high.

It is also known to bond various materials together utilizing radio frequency waves, i.e., dielectric bonding, wherein the material to be bonded acts as a dielectric between metallic elements of the bonding machinery. In this process heat is generated from the interior of the dielectric and flows outwardly in a manner similar to a microwave oven. When apparatus used for performing this process is utilized in conjunction with bonding of synthetic hook and loop fastener elements to fabric, the heat generated is such that burning of the fabric or melting of the synthetic hook and loop fastener elements occurs and this process cannot be utilized for producing conventional fastening straps.

Furthermore, since fastening straps of the type under consideration are used by individuals of various frame and structural sizes, the straps produced by the conventional ultrasonic means are manufactured in various sizes which must be stocked by the sellers. This creates large inventories of a relatively inexpensive product. The bond provided by the ultrasonic process is a spot or tack bond and the straps cannot be readily cut by the end user without fraying of the edges of the fabric material, especially if cut remote from a tack.

SUMMARY OF THE INVENTION

Accordingly, the present invention overcomes the problems of the prior art and permits the use of dielectric bonding of synthetic hook and loop fastener elements to a backing to form laminated fastening straps. Since dielectric means are utilized, multiple dies may be ganged to permit simultaneous production of a number of such straps. The strap of the present invention comprises a plastic backing—vinyl—to which the synthetic hook and loop fastener elements are bonded along the borders of the strap and across the strap at desired locations. Although the vinyl backing is a more expensive material than the plain hook and loop fabric generally used, it permits ganging of dies and thus a lower overall product cost. By bonding the synthetic hook and loop fastener elements to the vinyl in a diagonal or zig zag manner across the strap along at least a portion of the length thereof, the straps may be manufactured in a standard size and subsequently cut along a desired diagonal to provide straps of the required length. The diagonally extending bond permits cutting without fraying and without separation of the fastening elements from the backing.

Consequently, it is a primary object of the present invention to provide a fastening strap for use with orthopedic appliances and the like which has synthetic hook and loop fastener elements bonded to a vinyl backing.

It is another object of the present invention to provide a fastening strap for use with orthopedic appliances and the like having synthetic hook and loop fastener elements laminated to a vinyl backing along the border of the straps and along angularly extending bond lines which may be cut selectively as required for various size requirements.

BRIEF DESCRIPTION OF THE DRAWINGS

The particular features and advantages of the invention as well as other objects will become apparent from the following description taken in connection with the accompanying drawings, in which.

DESCRIPTION OF THE PREFERRED EMBODIMENT

Figure 1:
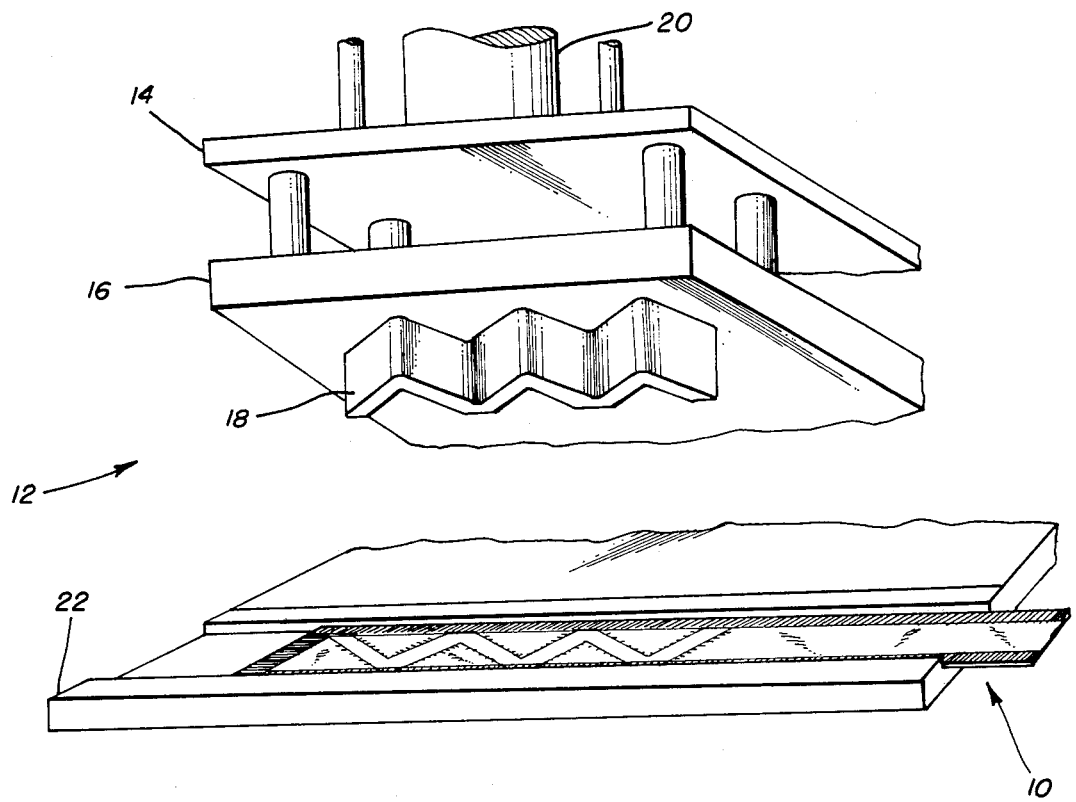
FIG. 1 is a generally diagrammatic view of a portion of a dielectric bonding apparatus used for producing a laminated fastening strap constructed in accordance with the principles of the present invention.
Figure 4:
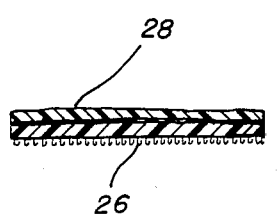
FIG. 4 is a cross sectional view taken substantially along line 4—4 of FIG. 2.
Figure 3:
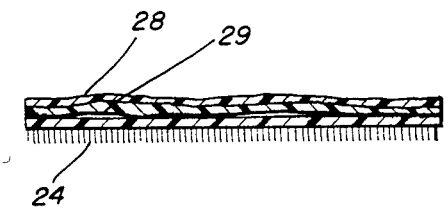
FIG. 3 is a cross sectional view taken substantially along line 3—3 of FIG. 2.

Referring now to the drawings, a strap 10 constructed in accordance with the principles of the present invention is produced by utilizing dielectric bonding apparatus 12 such as that illustrated in FIG. 1. The apparatus may comprise a press 14 reciprocably carrying an electrically conductive metal head 16 which in turn carries dies such as that illustrated at 18. The press is reciprocated vertically by means of a ram 20 to drive the dies downwardly into engagement with the strap to be laminated which is supported in the die cavity disposed on a metal shuttle 22. When the dies engage the strap in the cavity, the high frequency (e.g., in the radio frequency range, such as approximately 28 megacycles)

electrical energy acting between the dies in the head 16 and the respective cavity in the shuttle 22 acts to bond the plies of the strap together by the heat generated in the plies to be laminated, the latter acting as a dielectric. Using this proceedure a number of dies may be ganged together in the head 16 and cooperate with a like number of die cavities in the shuttle to simultaneously produce a number of straps.

The strap is formed from a laminate having on one surface thereof synthetic hook and loop fastener elements such as is known in the trade as "Velcro" or similar material comprising a plastic sheet having a myriad of closely spaced synthetic plastic hooks 24 and loops 26 and which when pushed or squeezed together interlock to form a strong connection between the hook and loop elements at selected adjustable positions which resist separation by a pull in the plane of the interacting parts, but which may be pulled apart by a separating pull on an end of one of the parts at an angle to said plane. A substantial longitudinally extending portion of the fastening surface of the strap has the hook elements while the remainder carries the loop elements. In use as a face strap one portion is riveted or the like to an orthopedic garment and the other portion is inserted through a ring and looped back into fastening relationship with the first portion. When used as a back strap the strap is merely wrapped around without the ring.

The other surface of the laminate according to the present invention comprises a backing 28 of vinyl, and intermediate the synthetic hook and loop fastener elements and the backing there may be a heat activated adhesive film 29 such as U-740 manufactured and distributed by General Fabric Fusing, Inc. of Cinncinnati, Ohio, which may be a separate sheet or precoated onto the back of the hooked loop elements. The dies engage the vinyl backing while the synthetic hook and loop fastener elements are disposed in the cavities with the adhesive between the plys. The heat generated flows from the inside outwardly and bonds the vinyl backing to the fastener elements along the portions of the die which engage the backing. In so doing the dies indent or recess the vinyl material at the bonded joints.

Figure 2:
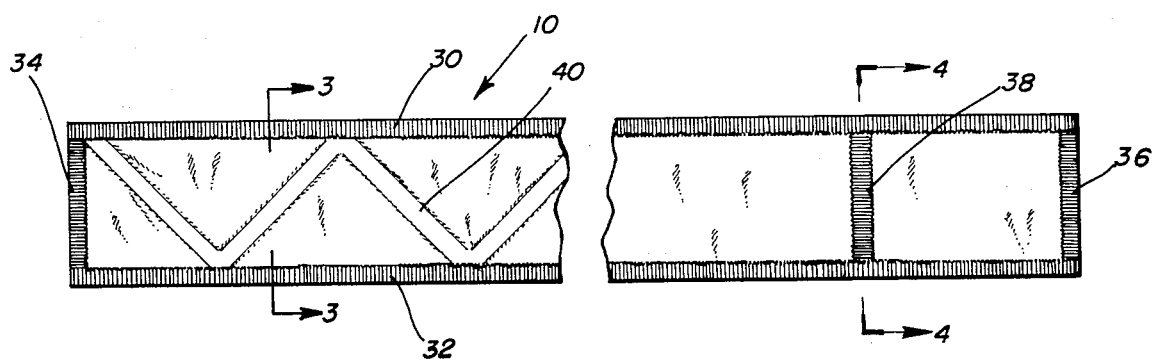
FIG. 2 is a top plan view of the strap illustrating the backing surface.

As illustrated in FIG. 2, the backing 28 is bonded to the synthetic hook and loop fastener elements along the longitudinal borders 30, 32 and the ends 34, 36 of the strap. This provides a sufficient bond for most straps but additional bonding may occur transverse to the borders 30, 32 such as at 38 to increase the holding power of the bond and/or for aesthetic appeal. Furthermore, preferably the plies are additionally bonded along angularly extending bond lines or areas 40 between the borders 30, 32 in diagonal or zig zag fashion for a portion of the strap. The bond areas 40 are of a sufficient width such that a cut through the vinyl and the fastening material along a central portion of a bond area to shorten the strap will not disturb the bond remaining along the cut. Thus, the strap may be shortened as desired without separation of the plies at the end of the strap and without fraying of the material forming the plies. Moreover, the leading edge of a diagonal can be readily inserted through a ring on an orthopedic appliance. This provides the advantage that the straps may be made in convenient lengths and cut to the required length needed thereby reducing the requirement to inventory and store large number of straps of varying sizes.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A laminated fastening strap for use with orthopedic appliances and the like for adjustably securing the appliance to the body of a user, said strap comprising an elongated laminate having first and second plies of material bonded together, said first ply comprising a plastic sheet having hook and loop fastener elements extending from a single surface thereof, the hooks extending from one end of the strap toward the other end and the loops extending from the other end toward the hooks, said second ply comprising a vinyl sheet of the same size as the first ply, said plies being joined together in a bond along common borders defining the edges of the strap and areas adjacent said edges.

2. A strap as recited in claim 1, wherein said plies are joined together along additional bonded areas extending intermediate the longitudinally extending borders of the strap.

3. A strap as recited in claim 2, wherein said additional areas include areas extending angularly relative to said longitudinally extending borders in zig zag fashion so that said strap may be shortened to desired lengths by cutting through said strap in a selected angularly extending area.

4. A strap as recited in claim 3, wherein each of said areas in the vinyl sheet is indented.

5. A strap as recited in claim 3, wherein the joints between said plies are fused together by heat.

* * * * *